United States Patent [19]

Lee

[11] 4,230,871

[45] Oct. 28, 1980

[54] PROCESS FOR PREPARING 5,6-DIHYDRO-2-METHYL-1,4-OXATHIIN DERIVATIVES

[76] Inventor: Wha S. Lee, c/o 678 Portage St., Ottawa, Canada, K1G 1T4

[21] Appl. No.: 25,834

[22] Filed: Apr. 2, 1979

Related U.S. Application Data

[63] Continuation of Ser. No. 839,129, Oct. 3, 1977, abandoned.

[51] Int. Cl.³ ........................................... C07D 327/06
[52] U.S. Cl. ....................................................... 549/14
[58] Field of Search ...................... 260/327 P; 549/14

[56] References Cited

PUBLICATIONS

G. Edwin Wilson, Jr., Jour. Am. Chem. Soc., vol 87, No. 16, Aug. 20, 1965, pp. 3785-3786.
G. Edwin Wilson, Jr. et al, J. Org. Chem., vol. 41, No. 6 (1976) pp. 966-968.

*Primary Examiner*—Norma S. Milestone
*Attorney, Agent, or Firm*—Richard J. Hicks; Stanley E. Johnson

[57] ABSTRACT

5,6-Dihydro-2-methyl-1,4-oxathiin derivatives are prepared by chlorinolysis of an appropriate 1,3-oxathiolane derivative to generate alkene-sulfenyl chloride, followed by cyclization and loss of hydrogen chloride to form said product.

3 Claims, No Drawings

PROCESS FOR PREPARING 5,6-DIHYDRO-2-METHYL-1,4-OXATHIIN DERIVATIVES

This is a continuation of application Ser. No. 839,129 filed Oct. 3, 1977 now abandoned.

This invention relates to a new and improved method of preparing 5,6-dihydro-2-methyl-1,4-oxathiin derivatives(I) represented by the formula

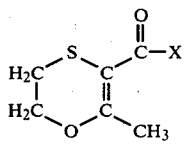

wherein X is an amino or alkoxy group. The amino group may be primary, secondary or tertiary, and the alkyl moiety of the alkoxy group may be primary, secondary or tertiary. It is apparent that the derivatives I may represent 5,6-dihydro-2-methyl-1,4-oxathiin-3-carboxamides(Ia) when X is the amino group, and 5,6-dihydro-2-methyl-1,4-oxathiin-3-carboalkoxides(Ib) when X is the alkoxy group.

The compounds Ia and Ib are known chemicals having been described in U.S. Pat. Nos. 3,249,499 (May 3, 1966), 3,393,202 (July 16, 1968), and in Can. Pat. Nos. 787,893 (June 18, 1968), 791,151 (July 30, 1968). 5,6-Dihydro-2-methyl-1,4-oxathiin-3-carboxamides (Ia) have been described as having fungicidal and bactericidal properties. The compounds Ib are also useful chemicals as these can be converted to compounds Ia.

The prior art preparation of 5,6-dihydro-2-methyl-1,4-oxathiin-3-carboxamides(Ia) has been effected by two methods. The first method has included (1) converting acetoacetamide to alphachloroacetoacetamide, (2) reacting this with 2-mercaptoethanol in a mutual solvent in the presence of a base; (3) subjecting the resulting product to acidic conditions whereby it cyclizes with loss of water to form 5,6-dihydro-2-methyl-1,4-oxathiin-3-carboxamide(Ia) and (4) isolating said product from the reaction mixture. The second method of preparing same has used alkyl acetoacetate in place of acetoacetamide as a starting material. Thus, from the procedure analogous to the first method described above, the resulting 5,6-dihydro-2-methyl-1,4-oxathiin-3-carboalkoxide(Ib) was converted to 5,6-dihydro-2-methyl-1,4-oxathiin-3-carboxamide(Ia).

Prior art process as generally outlined is subject to certain disadvantage. One disadvantage of the prior art process is that the first method described above is sensitive to side reaction and the yields of 5,6-dihydro-2-methyl-1,4-oxathiin-3-carboxamides (Ia) obtained by such method are lower than desired. Another disadvantage is that, in the first and second methods described above, the preparation of alpha-haloacetoacetamide or alkyl alpha-haloacetoacetate is somewhat inconvenient step, and overall yield of 5,6-dihydro-2-methyl-1,4-oxathiin-3-carboxamide(Ia) via the second method is relatively low.

It is an object of the present invention to provide a new and improved method for preparing 5,6-dihydro-2-methyl-1,4-oxathiin derivatives(I).

SUMMARY OF THE INVENTION

These and other objects of the present invention are achieved in accordance with the present invention which provides a novel process of preparing 5,6-dihydro-2-methyl-1,4-oxathiin derivatives (I) comprising the steps of: (1) reacting acetoacetamide or alkyl acetoacetate with 2-mercaptoethanol(II) in the presence of a acid catalyst to form 1,3-oxathiolane derivative IV, (2) subjecting IV to chlorinolysis whereby ring expansion takes place via alkene-sulfenyl chloride intermediate V which cyclizes with loss of hydrogen chloride to form compound I.

DETAILED DESCRIPTION OF THE INVENTION

A new process for the preparation of 5,6-dihydro-2-methyl-1,4-oxathiin derivatives(I) has been discovered. The process, represented by the following equations, involves preparing the appropriate 1,3-oxathiolane derivatives IV, and then subjecting these sulfides to halogenolysis.

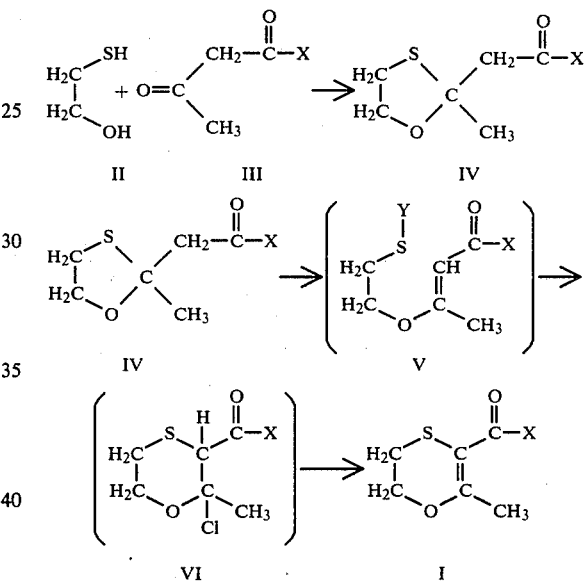

In the above equations X is a primary, secondary or tertiary amino group, or X is an alkoxy group in which the alkyl moiety is primary, secondary or tertiary, and Y is chlorine or bromine. 1,3-Oxathiolane derivative IV, which is an ethylene hemithioketal of the carbonyl compound III, can be prepared by reacting acetoacetamide(III, e.g., X=$C_6H_5NH$) or alkyl actoacetate (III, e.g., X=OEt) with 2-mercaptoethanol(II) in the presence of a acid catalyst in a refluxing solvent such as benzene or ether. The ring expansion reaction can be conducted by treating 1,3-oxathiolane derivative IV with 1 equivalent of chlorine (it will be understood that bromine may be used instead) in methylene chloride, chloroform or carbon tetrachloride at a temperature of about −60° to room temperature. The reaction proceeds through intermediates V and VI, neither of which need be isolated. The internal alkene-sulfenyl chloride intermediate V readily cyclizes to VI. The intermediate VI is dehydrohalogenated readily with or without a base to yield the product I.

The following examples illustrate in more detail the practice of the invention. It will be understood that the invention is not confined to the specific limitations set forth in the following examples but rather, to the scope of the appended claims.

EXAMPLE 1

Preparation of 2-methyl-2-carboxanilidomethyl-1,3-oxathiolane (IV, X=C₆H₅NH)

A solution of acetoacetanilide(17.72 g., 0.1 mole), 2-mercaptoethanol(7.81 g., 0.1 mole) and p-toluenesulfonic acid monohydrate(0.16 g.) in anhydrous benzene(40 ml.) was refluxed in a round bottomed flask connected to a Dean-Stark water separator for 5 hr. until no more water appeared in the separator. The water collected was 1.8 ml.(theory 1.8 ml.). The benzene solution was cooled, washed with sodium bicarbonate solution and water, dried(MgSO₄) and decolorized(charcoal). Solvent was evaporated at 40° under reduced pressure to give gummy residue(24,7 g.). The residue was crystallized from ethyl acetate-petroreum ether to obtain colorless short needles(21.4 g., 90.2%); m.p. 85°-87°.

EXAMPLE 2

Preparation of 2-methyl-2-carboethoxymethyl-1,3-oxathiolane (IV, X=OEt)

Method A.

A solution of ethyl acetoacetate(13.02 g., 0.10 mole) and 2-mercaptoethanol(7.81 g., 0.10 mole) in anhydrous benzene (40 ml.) containing 0.16 g. of p-toluenesulfonic acid monohydrate was refluxed in a round bottomed flask connected to a Dean-Stark water separator for 4 hr. until no more water appeared in the separator. The water collected was 1.8 ml.(theory 1.8 ml.). The benzene solution was cooled, washed with sodium bicarbonate solution and with water, and dried(MgSO₄). Solvent was evaporated at room temperature under reduced pressure to obtain colorless oily residue(17.38 g., 91.30%).

Method B.

To a stirred and refluxing solution of ethyl acetoacetate (32.54 g., 0.25 mole) and 2-mercaptoethanol(19.53 g., 0.25 mole) in anhydrous ether(200 ml.) was added BF₃·Et₂O(35.48 g., 0.25 mole) dropwise over 1 hr. The mixture was allowed to reflux for an additional hour. The resulting reaction mixture was cooled, washed with sodium bicarbonate solution and water, and dried(MgSO₄). Solvent was evaporated at room temperature under reduced pressure to give colorless oily residue(42.1 g., 88.48%).

EXAMPLE 3

Preparation of 5,6-dihydro-2-methyl-1,4-oxathiin-3-carboxanilide (Ia=C₆H₅NH)

To a stirred solution of 1,3-oxathiolane(IV, X=C₆H₅NH) (0.500 g., 0.00211 mole) in methylene chloride(20 ml.) cooled in the acetone-dry ice bath at −40° was added dropwise a solution of chlorine(0.15 g., 0.00211 mole) in methylene chloride(9.6 ml.) over 10 mins. After stirring at the same temperatue for 1 hr., triethylamine(0.426 g., 0.00422 mole) was added, and stirring was continued for an additional hour. The bath was removed and the reaction mixture was washed with sodium bicarbonate solution and water, and dried(Na₂SO₄). Solvent was evaporated at room temperature to obtain oily residue(0.5178 g.), crystallized from ethyl acetate-petroleum ether giving(0.398 g., 80.5%). Ia(X=C₆H₅NH). Nmr(CDCl₃): δ2.24(s, 3H), 2.92(t, 2H), 4.34(t, 2H), 6.96-7.54(m, 5H), 7.94(s,1H). This product is identical in every respect to that prepared by the previously known method [U.S. Pat. No. 3,393,202(July 16, 1968)] [Note]: In the above patent compound Ia(X=C₆H₅NH) was alternatively named 2,3-dihydro-5-carboxanilido-6-methyl-1,4-oxathiin.

EXAMPLE 4

Preparation of 5,6-dihydro-2-methyl-1,4-oxathiin-3-carboethoxide (Ib, X=OEt)

To stirred solution of 1,3-oxathiolane(IV, X=OEt) (1.000 g., 0.00526 mole) in methylene chloride(20 ml.) in the acetone-dry ice bath at −20° was added a solution of chlorine(0.373 g., 0.00526 mole) in methylene chloride (12 ml.) over 10 mins. The stirring was continued for 1 hr. at the same temperature and for an additional 1 hr. after removing the bath. The resulting reaction mixture was washed with sodium bicarbonate solution and with water and dried (Na₂SO₄). Solvent was evaporated at room temperature under reduced pressure to obtain pale yellow oily liquid residue(0.841 g., 85.0%). Nmr(CDCl₃): δ1.29(t, 3H), 2.30(s, 3H), 2.94(t, 2H), 4.20(q, 2H), 4.32(t, 2H). The product is identical in every respect to that prepared by the previously known method [U.S. Pat. No. 3,393,202 (July 16, 1968)] [Note]: In the above patent the compound Ib(X=OEt) was alternatively named ethyl 2,3-dihydro-6-methyl-1,4-oxathiin-5-carboxylate.

I claim:

1. A process of preparing 5,6-dihydro-2-methyl-1,4-oxathiin derivative I of the formula

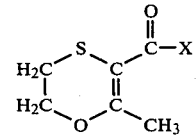

wherein X is an amino group having the formula,

wherein R and R' are the same or different and are selected from the group consisting of hydrogen, phenyl, alkyl having up to 15 carbon atoms, cyclohexyl, nitrophenyl, alkoxyphenyl in which the alkoxy group has up to 4 carbon atoms, benzyl, furfuryl, halophenyl, tolyl, naphthyl, biphenyl, or X is an alkoxy group—OR, in which R is primary, secondary or tertiary alkyl group having up to 6 carbon atoms; comprising treating the 1,3-oxathiolane IV of the formula:

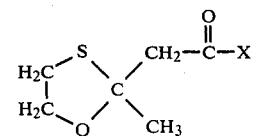

wherein X is the same as in the formula I, with halogen (chlorine or bromine) in a nonhydroxylic solvent at a temperature in the range between −60° C. and room temperature whereby ring expansion takes place via a sulfenyl compound of the formula

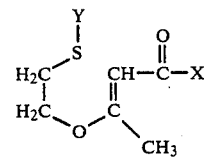

wherein Y is Cl or Br which cyclizes with loss of hydrogen halide to form the compound I, and subsequently isolating this from the resulting mixture.

2. A process as claimed in claim 1 wherein said derivative I is prepared by reacting compound IV wherein X=OEt with chlorine at a temperature of −20° C.

3. A process as claimed in claim 1 wherein said derivative I is prepared by reacting compound IV wherein X=NHC$_6$H$_5$ with chlorine at a temperature of −40° C.

* * * * *